United States Patent [19]

Jaraczewski et al.

[11] Patent Number: 5,445,148
[45] Date of Patent: Aug. 29, 1995

[54] INTRACARDIAC ELECTRICAL POTENTIAL REFERENCE CATHETER

[75] Inventors: Richard Jaraczewski, Livermore; Scott West, Tracy, both of Calif.

[73] Assignee: Medtronic CardioRhythm, San Jose, Calif.

[21] Appl. No.: 138,557

[22] Filed: Oct. 15, 1993

Related U.S. Application Data

[63] Continuation-in-part of Ser. No. 866,763, Apr. 10, 1992, abandoned.

[51] Int. Cl.$^6$ ................................................ A61B 5/04
[52] U.S. Cl. ..................................................... 128/642
[58] Field of Search ................ 128/642, 673; 607/119, 607/120, 122, 123; 604/264, 280, 282; 606/46

[56] References Cited

U.S. PATENT DOCUMENTS

| | | | |
|---|---|---|---|
| 4,135,518 | 1/1979 | Dutcher | 128/642 |
| 4,660,571 | 4/1987 | Hess et al. | 128/642 |
| 4,682,603 | 7/1987 | Franz . | |
| 4,695,276 | 9/1987 | Shinno et al. | 604/283 |
| 4,699,157 | 10/1987 | Shonk . | |
| 4,777,955 | 10/1988 | Brayton et al. | 128/642 |
| 4,882,777 | 11/1989 | Narula | 604/281 |
| 4,920,980 | 5/1990 | Jackowski | 128/786 |
| 4,940,064 | 7/1990 | Desai | 128/786 X |
| 4,953,564 | 9/1990 | Berthelsen | 128/642 |
| 4,955,382 | 9/1990 | Franz et al. . | |
| 4,960,134 | 10/1990 | Webster, Jr. | 128/642 |
| 4,979,510 | 12/1990 | Franz et al. | 128/786 |
| 5,057,092 | 10/1991 | Webster, Jr. | 604/282 |
| 5,069,217 | 12/1991 | Fleischhacker, Jr. | 604/280 X |
| 5,154,705 | 10/1992 | Fleischhacker et al. | 604/282 |
| 5,176,661 | 1/1993 | Evard et al. | 604/282 |
| 5,201,903 | 4/1993 | Corbett, III et al. | 607/57 X |
| 5,242,441 | 9/1993 | Avitall | 128/642 X |
| 5,318,041 | 6/1994 | DuBois et al. | 607/119 |

FOREIGN PATENT DOCUMENTS

| | | |
|---|---|---|
| 0476807 | 3/1992 | European Pat. Off. . |
| 3642107 | 6/1987 | Germany . |

*Primary Examiner*—Lee S. Cohen
*Assistant Examiner*—Samuel Gilbert
*Attorney, Agent, or Firm*—Townsend and Townsend Khourie and Crew

[57] ABSTRACT

An intracardiac electrical potential reference catheter includes a proximal shaft section in a distal flexible tip section. The flexible tip section shaped in a geometry suitable for performing intracardiac mapping and includes a plurality of electrode axially spaced-apart thereon. The shaft section is formed from a polymeric material and includes a reinforcement layer, typically a stainless steel braid. The flexible tip section is also formed from a polymeric material and is free from any braided reinforcement. A core wire is attached to a proximal housing on the catheter at one end and to a distal electrode tip at the other end. In this way, the torque is transmitted along the length of the catheter by both the reinforced shaft and separately by the core wire.

20 Claims, 2 Drawing Sheets

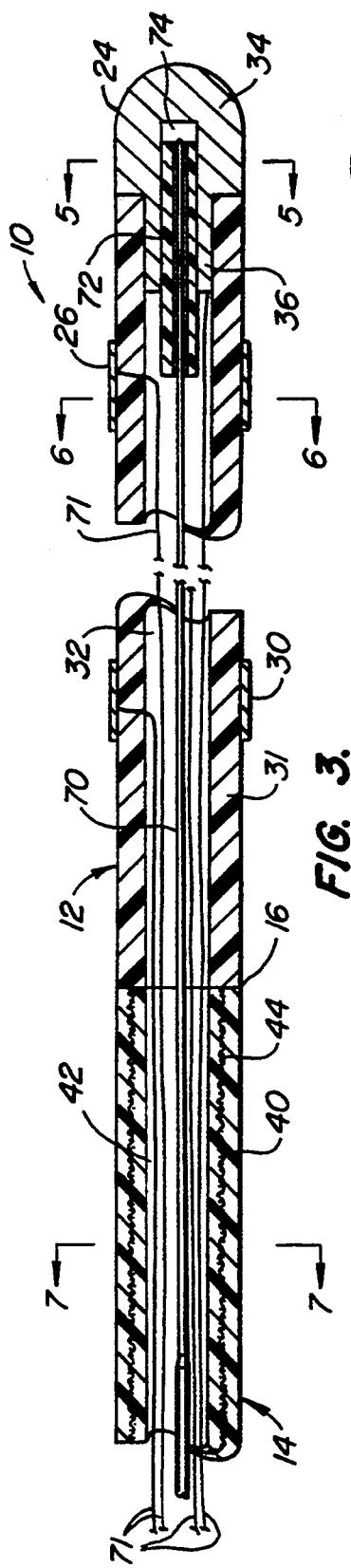
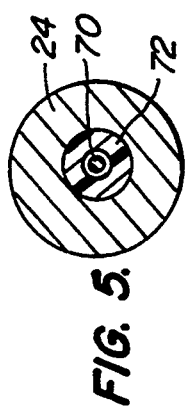
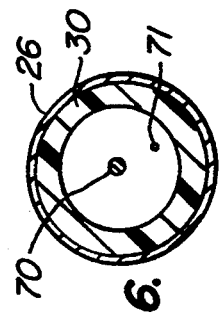
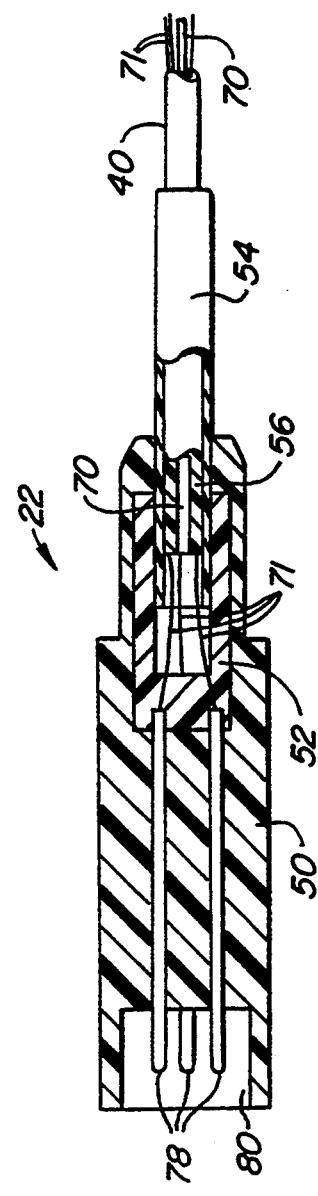

INTRACARDIAC ELECTRICAL POTENTIAL REFERENCE CATHETER

This is a Continuation-in-part of application Ser. No. 07/866,763 filed Apr. 10, 1992, now abandoned.

The present application is related to application Ser. No. 07/866,383 now U.S. Pat. No. 5,318,525, Ser. No. 07/866,683, filed on the same date as the present application. The disclosures of all of these co-pending applications are incorporated herein by reference.

BACKGROUND OF THE INVENTION

1. Field of the Invention

The present invention relates generally to the field of electrophysiology. More particularly, this invention relates to methods and apparatus for mapping cardiac arrhythmias.

Symptoms of abnormal heart rhythm are generally referred to as cardiac arrhythmias, with an abnormally slow rhythm being classified as bradycardia and an abnormally rapid rhythm being referred to as tachycardia. The present invention is concerned with the treatment of tachycardias which are frequently caused by the presence of an "arrhythmogenic site" or "accessory atrioventricular pathway" close to the inner surface of one of the chambers of the heart. The heart includes a number of normal pathways which are responsible for the propagation of signals necessary for normal electrical mechanical function. The presence of arrhythmogenic sites or accessory pathways can bypass or short circuit the normal pathways, potentially resulting in very rapid heart contractions, referred to as tachycardias. Tachycardias may be defined as ventricular tachycardias (VT's) and supraventricular tachycardias (SVT's). VT's originate in the left or right ventricle and are typically caused by arrhythmogenic sites associated with a prior myocardial infarction. SVT's originate in the atria and are typically caused by an accessory pathway.

Treatment of both ventricular and supraventricular tachycardias may be accomplished by a variety of approaches, including drugs, surgery, implantable pacemakers/defibrillators, and catheter ablation. While drugs may be the treatment of choice for many patients, they only mask the symptoms and do not cure the underlying cause. Implantable devices only correct the arrhythmia after it occurs. Surgical and catheter-based treatments, in contrast, will actually cure the problem, usually by ablating the abnormal arrhythmogenic tissue or accessory pathway responsible for the tachycardia. The catheter-based treatments rely on the application of various destructive energy sources to the target tissue, including direct current electrical energy, radiofrequency electrical energy, laser energy, and the like.

Regardless of the particular catheter-based treatment selected, it will generally be necessary to initially map the interior surfaces of the heart to locate the arrhythmogenic site(s) and accessory pathway(s). Such mapping involves the measurement of electrical potentials at different locations within the heart to detect abnormalities using a procedure generally referred to as "programmed electrical stimulation." A catheter having a series of axially spaced-apart electrodes near its distal end is introduced to the interior of the heart, and pacing of the heart is induced using certain pairs of the electrodes, usually the distal pair. Progression of the induced signal within the heart is monitored using the remaining pairs of electrodes which are connected to conventional ECG monitoring equipment. In this way, the locations of the arrhythmogenic sites and accessory pathways can be generally determined. Usually, the locations will be more specifically determined prior to treatment using the treatment catheters themselves. Treatment catheters are usually steerable and have reference electrodes which can be more precisely positioned.

The reference electrode catheters used for ECG mapping have distal tips which are shaped to lie in preselected configurations within the heart chamber being mapped. It is thus necessary that the distal tip of the catheter be manipulable from the proximal end so that the distal tip can be properly oriented after it has been introduced to the chamber. In particular, the treating physician must be able to rotate the distal end of the catheter about its longitudinal axis by applying a rotational torque to the proximal end of the catheter. Thus, the reference electrode catheters must be torsionally stiff to transmit the encessary rotational force along their lengths. The ability to transmit torque along the catheter, however, must be achieved without significant loss of axial flexibility of the catheter, particularly at its distal end. It will be appreciated that the distal end of the catheter should remain soft and flexible in order to avoid injury to the heart. Previous catheter designs have attempted to meet these objectives but have not been completely satisfactory.

Thus, it would be desirable to provide improved reference electrode catheters having enhanced torsional stiffness without significant loss of axial flexibility, particularly at the distal tip region. Such catheters should have a relatively simple construction, with a reduced member of components and materials.

2. Description of the Background Art

A left ventricle mapping probe having a plurality of spaced-apart band electrodes is described in U.S. Pat. No. 4,777,955. A cardiac pacing catheter having a distal tip electrode and an electrically conductive torque member in a central lumen filled with solid polymer is described in U.S. Pat. No. 4,699,157. Intracardiac catheters for recording monophasic action potentials in a heart and including a distal tip electrode and one or more side electrodes are described in U.S. Pat. Nos. 4,979,510; 4,955,382; and 4,682,603.

SUMMARY OF THE INVENTION

According to the present invention, an intracardiac electrical potential reference catheter having enhanced torsional stiffness and axial flexibility comprises a catheter body including both a shaft section having a proximal end, a distal end, and a lumen therethrough, and a flexible tip section having a proximal end, a distal end, and a lumen therethrough. The proximal end of the tip section is secured to the distal end of the shaft section so that the lumens are generally coaxially aligned. A tip electrode is secured to the distal end of the flexible tip section, and at least one additional band electrode is mounted on the exterior of the tip section spaced-apart proximally from the tip electrode. Usually, at least two additional band electrodes will be disposed on the flexible section, and as many as ten or more band electrodes may be provided. The catheter further includes a proximal connector housing secured to the proximal end of the shaft section, and the tip and band electrodes are connected to an electrical connector fitting on the housing, typically by wires running through the lumens.

The torsional stiffness of the catheter is enhanced in two ways. First, the shaft is a composite, comprising a polymeric tube reinforced with a braided layer, typically being composed of a thermoplastic material reinforced with a stainless steel braid. Second, a core wire extends from the proximal housing through the lumens of the shaft and the flexible tip sections, being fixedly secured to both the proximal housing and to the distal tip electrode. In this way, torque is efficiently transmitted to the tip section both by the reinforced shaft section and by the core wire which transmits torque directly from the proximal housing to the distal electrode tip. Use of the core wire permits the flexible tip section to be formed from a low durometer (soft) polymeric material, without reinforcement, so that the tip may be axially flexible while having sufficient torsional stiffness (from the core wire) to permit the necessary torsional manipulation. By utilizing a tapered core wire having a reduced diameter near its distal end, the flexibility of the tip section can be further enhanced while still providing adequate torque transmissibility.

BRIEF DESCRIPTION OF THE DRAWINGS

FIG. 3 is a cross-sectional view of the distal portion of the catheter of FIG. 1.

FIG. 4 is a cross-sectional view of a proximal housing of the catheter of FIG. 1.

FIG. 5 is a transverse cross-sectional view of the distal end of the catheter of FIG. 1, taken along line 5—5 of FIG. 3.

FIG. 6 is a transverse cross-sectional view of the distal end of the catheter of FIG. 1, taken along line 6—6 of FIG. 3.

FIG. 7 is a transverse cross-sectional view of the shaft section of the catheter of FIG. 1, taken along line 7—7 of FIG. 3.

DESCRIPTION OF SPECIFIC EMBODIMENTS

Figure 1:
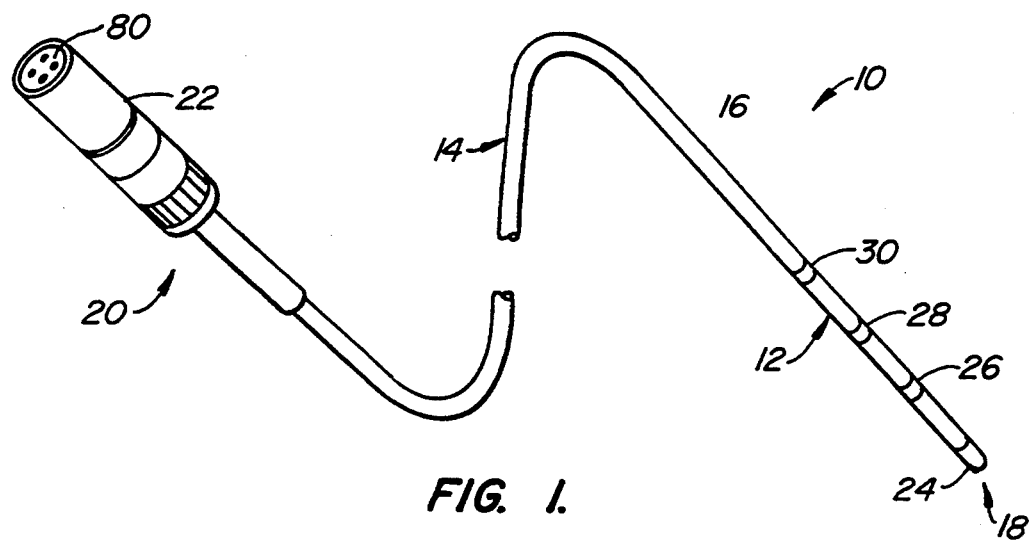
FIG. 1 is a perspective view of an electrical potential reference catheter constructed in accordance with the principles of the present invention.

Referring to FIG. 1, an electrical potential reference catheter 10 constructed in accordance with the principles of the present invention includes a flexible tip section 12 joined to a shaft section 14 at an attachment point 16. The reference catheter 10 has a distal end 18 and a proximal end 20, with an overall length typically in the range from about 60 cm to 150 cm with lengths of 80 cm and 125 cm being usual for subclavian and femoral entry, respectively. The flexible tip section 12 typically has a length in the range from about 1 cm to 10 cm, usually being about 5 cm, with the remaining length of the catheter being in the shaft section. A proximal housing 22 is secured to the proximal end 20 of the catheter 10.

A plurality of electrodes will be mounted on the tip section 12 of the catheter 10 in order to permit ECG mapping in the conventional manner. The electrodes will include a tip electrode 24 and at least one proximally spaced-apart band electrode 26. Usually, at least two additional band electrodes 28 and 30 will be provided, and the catheter may include up to a total of 10 or more electrodes. The spacing between electrodes is not critical, with adjacent electrodes usually being spaced from 2 mm to 1 cm apart, typically being about 5 mm apart. The spacing between adjacent electrodes may be the same or different, with a variety of particular spacing patterns being known in the art.

Figure 2A:
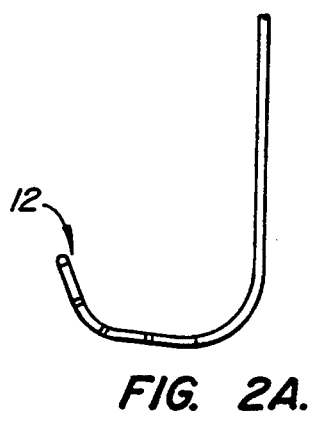
FIGS. 2A-2D illustrate various tip configurations of the electrical potential reference catheter of FIG. 1.
Figure 2B:
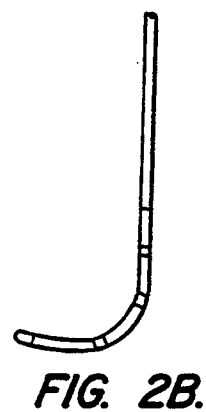
Figure 2C:
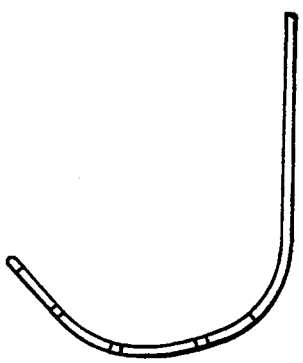
Figure 2D:
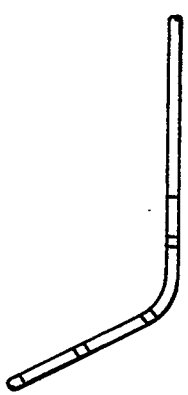

The distal portion of the catheter 10 will be shaped so that the catheter will align in a preselected conformation after introduction to a heart chamber. Usually, approximately 5 cm of the distal end of the catheter 10 will be shaped, including the entire flexible tip section 12 and a distal portion of the shaft section 14. As discussed below, both the flexible tip section 12 and shaft section 14 will be usually formed from a thermoplastic material, and shaping may be achieved by heating and molding in a conventional manner. Conventional tip configurations are illustrated in FIGS. 2A-2D, where the configuration of FIG. 2A is useful for mapping the HIS bundle; the configuration of FIG. 2B is useful for mapping according to the Josephson procedure; the configuration of FIG. 2C is useful for mapping the coronary sinus; and the configuration of FIG. 2D is useful for performing conduction studies.

Referring now to FIGS. 1 and 3, the flexible tip section 12 of catheter 10 comprises a polymeric tube 31 having a central lumen 32 extending therethrough. The polymeric tube 31 will be a low durometer thermoplastic, typically being a polyurethane tube having a durometer in the range from 30A to 75A and a wall thickness in the range from about 0.005 in. to 0.030 in. A suitable polymeric material for the flexible tip section 12 is Pellethane 2363 available from Dow Chemical Co., Midland, Mich. Other suitable materials for the polymeric tube 31 include nylon, polyether block copolymers (e.g., Peebax ®, Atochem, Germany), polyolefins (e.g., Hytrel ®, DuPont, Wilmington, Del.), and the like. Tip electrode 24 includes a bell-shaped distal section 34 and a shank section 36, where the shank is received in the distal end of the lumen 32 of the polymeric tube 30. Typically, the shank 36 is secured by an adhesive. The electrode 34 may be formed from any suitable electrode material, preferably being a platinum-iridium alloy. Band electrodes 26, 28, and 30 are disposed on the outside of the flexible tip section 12 and spaced proximally from the tip electrode 24, and may also be composed of a platinum-iridium alloy.

The shaft section 14 of catheter 10 is attached directly to the proximal end of the flexible tip section 12, typically by heat welding. The shaft section 14 comprises a polymeric tube 40 having a central lumen 42 which is coaxial with the lumen 32 of the flexible tip section 12. Polymeric tube 40 is reinforced with a braided layer 44, typically a stainless steel braid, where the braid characteristics, such as pick, angle, spacing, the nature of the strand (i.e. flat or round), and the like, can be selected to provide a desired torsional stiffness and axial flexibility. In an exemplary embodiment, the braid is 304 LV stainless steel formed from 0.003 in. diameter round strands at a 60° to 65° braid angle.

The polymeric tube 40 will be composed of a thermoplastic, typically having a hardness in the range from about 35 D to 75D. Usually, the composite of the thermoplastic tube and braided layer 44 will be fabricated by placing a first tube over the braided layer 44 and a second tube within the lumen of the braided layer, and then heating the composite structure so that the thermoplastic material impregnates the braid to form a unitary structure. An exemplary polymeric material is polyurethane, such as Pellethane 2363. Alternatively, the tube 40 may be formed in a continuous process where the thermoplastic is continuously extruded over the braided layer 44. Other suitable materials for the polymeric tube 70 include nylon, polyether block copolymers (e.g., Peebax ®, Atochem, Germany), polyolefins (e.g., Hytrel ®, DuPont, Wilmington, Del.), and the like.

Referring now to FIG. 4, the proximal housing 22 comprises an outer shell 50 having an internal collet 52 which receives a strain relief element 54. The proximal end 20 of the shaft 14 is received within the strain relief element 54 and, in turn, is clamped within the collet 52 and housing 50. Core wire 70 is fixed within the proximal end 20 of the shaft 14, typically by an adhesive matrix 56. In this way, torque applied to the housing 22 is transmitted directly to both the shaft 14 and to the core wire 42. The torque is then transmitted separately by each of the shaft 14 and core wire 42 through the length of the shaft and to the distal end 18 of the catheter. Connecting wires 71 are attached to pins 78 which form a connector plug at the proximal end of the housing 22.

A core wire 70 extends between the proximal housing 22 and the tip electrode 34, and is fixedly secured at each end. In particular, the core wire 70 is adhesively bonded in a sheath 72 disposed in a receptacle 74 within the shank 36 of the tip electrode 24. The polymeric sheath 72 provides an anchor point and electrical insulation between the core wire 70 and the tip electrode 24.

The core wire 70 is typically a metal wire, usually being a stainless steel wire having a diameter in the range from about 0.005 in. to 0.025 in. Preferably, the core wire 70 will be tapered (in stages or uniformly along its length), with a diameter at the proximal end in the range from 0.010 in. to 0.025 in. and at the distal end in the range from 0.005 in. to 0.015 in. The core wire 70 serves to directly couple the proximal portion of shaft 14 to the tip electrode 24 so that torque applied to the housing 22 will be transmitted directly to the extreme distal tip of the catheter 10. In addition to torque transmission through the core wire 70, the torque is also transmitted through the shaft section 14 of the catheter to the proximal end of the flexible tip section 12. By providing two separate torque transmitting elements within the catheter 10, improved torque transmission from the proximal end to the distal tip of the catheter is achieved without substantial loss of axial flexibility, particularly within the flexible tip section 12.

The plug assembly 80 at the proximal end of housing 22 permits connection of the catheter 10 to a standard ECG amplifier, such as those commercially available from a supplier such as Gould, E4M, and others. The connector 80 will include a number of pins corresponding to the number of electrodes to permit proper connection. Use of the catheter 10 and ECG mapping will be performed in a generally conventional manner.

Although the foregoing invention has been described in detail for purposes of clarity of understanding, it will be obvious that certain modifications may be practiced within the scope of the appended claims.

What is claimed is:

1. An electrical potential reference catheter comprising:
   a shaft having a proximal end, a distal end, and a lumen extending between said ends, wherein the shaft is a polymeric shaft tube having a braided reinforcement layer;
   a flexible tip section having a proximal end, a distal end, and a lumen extending between said ends, wherein the tip section is a polymeric tip tube and is fixedly attached at its proximal end to the distal end of the shaft;
   a tip electrode fixedly secured to the distal end of the flexible tip section;
   at least one additional band electrode proximally spaced-apart from the tip electrode on the flexible tip section;
   a proximal connector housing fixedly attached to the proximal end of the shaft;
   whereby said shaft and said tip section provide torque transmission directly from the housing to the tip electrode;
   a single core wire suspended generally coaxially in the lumens of the shaft and flexible tip section and extending between the proximal connector housing and the tip electrode and fixedly connected to both, wherein a distal end of the core wire is anchored coaxially within the tip electrode;
   whereby said core wire provides torque transmission directly from the housing to the tip electrode; and
   means for electrically connecting the electrodes to the proximal connector housing.

2. An electrical potential reference catheter as in claim 1 wherein the shaft tube is composed of a material selected from the group consisting of a polyurethane, a nylon, a polyethylene block copolymer, and a polyolefin having a durometer from 35D to 75D and wherein the braided reinforcement layer is a stainless steel reinforcement braid.

3. An electrical potential reference catheter as in claim 2, wherein the tip tube is composed of a material selected from the group consisting of a polyurethane, a nylon, a polyethylene block copolymer, and a polyolefin having a durometer from 30A to 75A.

4. An electrical potential reference catheter as in claim 3, wherein the core wire is stainless steel having a diameter from 0.005 in. to 0.025 in.

5. An electrical potential reference catheter as in claim 4, wherein the core wire has proximal and distal ends, the core wire being tapered, having a diameter from 0.015 in. to 0.025 in. at its proximal end and a diameter from 0.005 in. to 0.015 in. at its distal end.

6. An electrical potential reference catheter as in claim 1, further comprising a polymeric sheath tube extending into an axial receptacle in the tip electrode and receiving the core wire in order to provide electrical insulation of the core wire at the transition to the tip electrode.

7. An electrical potential reference catheter as in claim 6, wherein the polymeric sheath tube is composed of a polyimide.

8. An electrical potential reference catheter comprising:
   a shaft having a proximal end, a distal end, and a lumen extending between said ends, wherein the shaft is a polymeric shaft tube having a braided reinforcement layer;
   a flexible tip section having a proximal end, a distal end, and a lumen extending between said ends, wherein the tip section is a polymeric tip tube and is fixedly attached at its proximal end to the distal end of the shaft;
   a tip electrode fixedly secured to the distal end of the flexible tip section;
   at least one additional band electrode proximally spaced-apart from the tip electrode on the flexible tip section;
   a proximal connector housing fixedly attached to the proximal end of the shaft;

whereby said shaft and said tip section provide torque transmission directly from the housing to the tip electrode;

a core wire extending between the proximal connector housing and the tip electrode and fixedly connected to both;

whereby said core wire provides torque transmission directly from the housing to the tip;

a polymeric sheath tube extending into an axial receptacle in the tip electrode and receiving the core wire in order to provide electrical insulation of the core wire at the transition to the tip electrode; and means for electrically connecting the electrodes to the proximal connector housing.

9. An electrical potential reference catheter as in claim 8 wherein the shaft tube is composed of a material selected from the group consisting of a polyurethane, a nylon, a polyethylene block copolymer, and a polyolefin having a durometer from 35D to 75D with a stainless steel reinforcement braid.

10. An electrical potential reference catheter as in claim 9, wherein the flexible tip tube is composed of a material selected from the group consisting of a polyurethane, a nylon, a polyethylene block copolymer, and a polyolefin having a durometer from 30A to 75A.

11. An electrical potential reference catheter as in claim 10, wherein the core wire is stainless steel having a diameter from 0.005 in. to 0.025 in.

12. An electrical potential reference catheter as in claim 11, wherein the core wire has proximal and distal ends, the core wire being tapered, having a diameter from 0.015 in. to 0.025 in. at its proximal end and a diameter from 0.005 in. to 0.015 in. at its distal end.

13. An electrical potential reference catheter as in claim 8, wherein the polymeric sheath tube is composed of a polyimide.

14. An electrical potential reference catheter comprising:

a shaft having a proximal end, a distal end, and a lumen extending between said ends, wherein the shaft is a polymeric shaft tube having a braided reinforcement layer;

a flexible tip section having a proximal end, a distal end, and a lumen extending between said ends, wherein the tip section is a polymeric tip tube and is fixedly attached at its proximal end to the distal end of the shaft;

a tip electrode fixedly secured to the distal end of the flexible tip section;

at least one additional band electrode proximally spaced-apart from the tip electrode on the flexible tip section;

a proximal connector housing fixedly attached to the proximal end of the shaft;

whereby said shaft and said tip section provide torque transmission directly from the housing to the tip electrode;

a core wire extending between the proximal connector housing and the tip electrode and fixedly connected to both;

whereby said core wire provides torque transmission directly from the housing to the tip; and means for electrically connecting the electrodes to the proximal connector housing.

15. An electrical potential reference catheter as in claim 14 wherein the shaft tube is composed of a material selected from the group consisting of a polyurethane, a nylon, a polyethylene block copolymer, and a polyolefin having a durometer from 35D to 75D with a stainless steel reinforcement braid.

16. An electrical potential reference catheter as in claim 15, wherein the tip tube is composed of a material selected from the group consisting of a polyurethane, a nylon, a polyethylene block copolymer, and a polyolefin having a durometer from 30A to 75A.

17. An electrical potential reference catheter as in claim 16, wherein the core wire is stainless steel having a diameter from 0.005 in. to 0.025 in.

18. An electrical potential reference catheter as in claim 17, wherein the core wire has proximal and distal ends, the core wire being tapered, having a diameter from 0.015 in. to 0.025 in. at its proximal end and a diameter from 0.005 in. to 0.015 in. at its distal end.

19. An electrical potential reference catheter as in claim 14, further comprising a polymeric sheath tube extending into an axial receptacle in the tip electrode and receiving the core wire in order to provide electrical insulation of the core wire at the transition to the tip electrode.

20. An electrical potential reference catheter as in claim 19, wherein the polymeric sheath tube is composed of a polyimide.

* * * * *